(12) United States Patent
Lawrence et al.

(10) Patent No.: US 8,381,719 B1
(45) Date of Patent: Feb. 26, 2013

(54) MEDICAMENT DELIVERY SYSTEM WITH DOSE INDICATOR AND OVERSLEEVE ACTUATOR

(75) Inventors: Greg Lawrence, London (CA); Noel Gulka, London (CA)

(73) Assignee: Trudell Medical International, London (CA)

( * ) Notice: Subject to any disclaimer, the term of this patent is extended or adjusted under 35 U.S.C. 154(b) by 393 days.

(21) Appl. No.: 12/643,698

(22) Filed: Dec. 21, 2009

Related U.S. Application Data

(60) Provisional application No. 61/139,874, filed on Dec. 22, 2008.

(51) Int. Cl.
*A62B 17/04* (2006.01)

(52) U.S. Cl. .................................. 128/200.23

(58) Field of Classification Search ............. 128/200.14, 128/200.23, 204.23, 204.26, 202.22
See application file for complete search history.

(56) References Cited

U.S. PATENT DOCUMENTS

| | | | |
|---|---|---|---|
| 4,817,822 A | 4/1989 | Rand et al. | |
| 5,012,803 A | 5/1991 | Foley et al. | |
| 5,069,204 A | 12/1991 | Smith et al. | |
| 5,263,475 A | 11/1993 | Altermatt et al. | |
| 5,447,150 A * | 9/1995 | Bacon | 128/200.14 |
| 5,544,647 A | 8/1996 | Jewett et al. | |
| 5,622,163 A | 4/1997 | Jewett et al. | |
| 5,904,139 A * | 5/1999 | Hauser | 128/200.23 |
| 6,082,358 A | 7/2000 | Scarrott et al. | |
| 6,234,168 B1 | 5/2001 | Bruna | |
| 6,328,037 B1 | 12/2001 | Scarrott et al. | |
| 6,336,453 B1 | 1/2002 | Scarrott et al. | |
| 6,516,799 B1 | 2/2003 | Greenwood et al. | |
| 6,701,917 B2 | 3/2004 | O'Leary | |
| 6,729,330 B2 | 5/2004 | Scarrott et al. | |
| 6,769,601 B2 | 8/2004 | Haikarainen et al. | |
| 7,004,164 B2 | 2/2006 | Scarrott | |

FOREIGN PATENT DOCUMENTS

WO    WO 93/24167 A1    12/1993

* cited by examiner

*Primary Examiner* — Manuel Mendez
(74) *Attorney, Agent, or Firm* — Brinks Hofer Gilson & Lione

(57) ABSTRACT

A delivery assembly for dispensing a medicament from a container includes a dispenser housing having a longitudinally extending peripheral wall defining an interior surface. A container includes a canister having first and second ends and an exterior surface spaced from the interior surface of the dispenser housing so as to form a gap therebetween. A dose indicator is disposed on the second end of the canister and includes dosage indicia. A sleeve is disposed over the dose indicator and includes a longitudinally extending wall disposed in the gap between the interior surface of the dispenser housing and the exterior surface of the canister. The sleeve is reciprocally moveable relative to the canister and to the dispenser housing. A medicament delivery kit, a method of dispensing medicament from a medicament delivery device and a method of assembling a medicament delivery device also are provided.

26 Claims, 5 Drawing Sheets

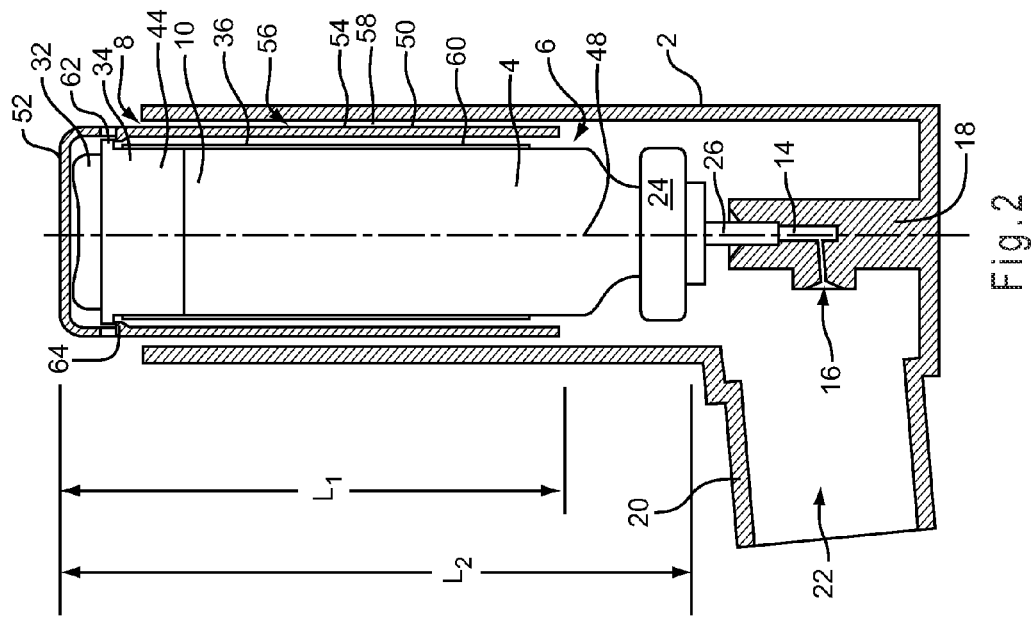
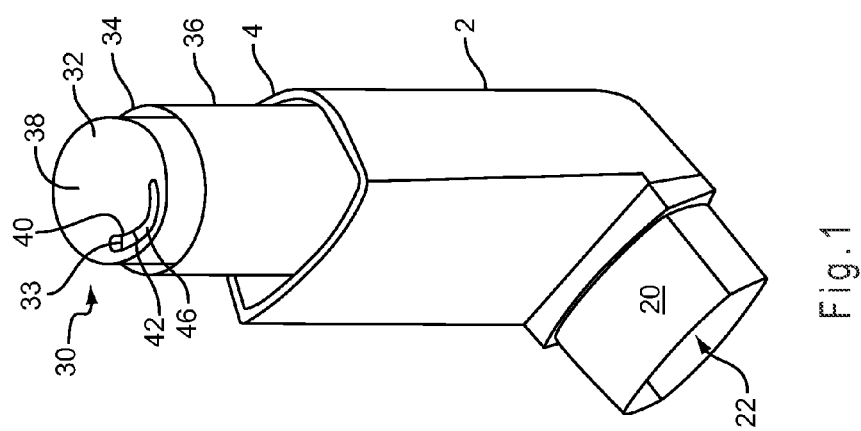

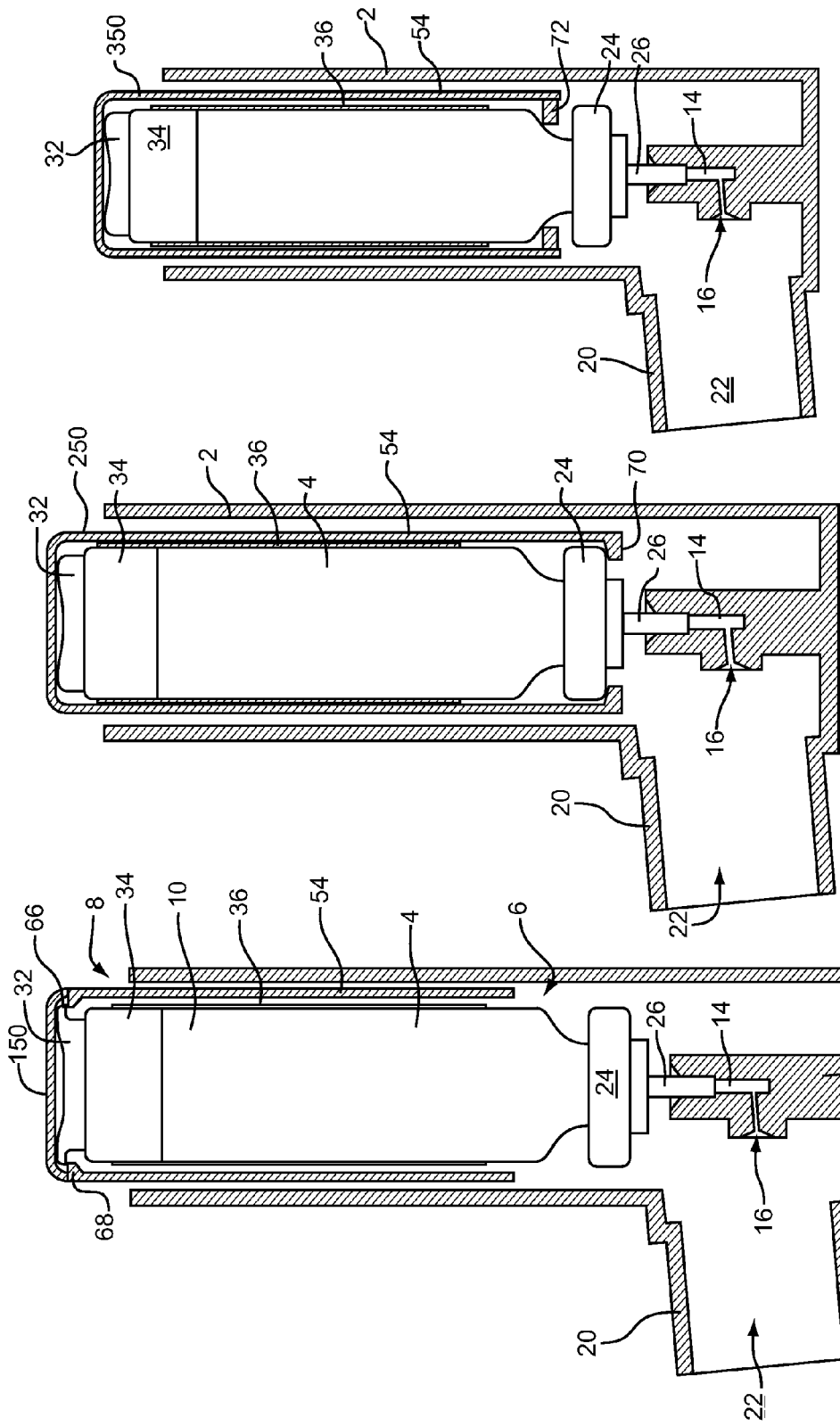

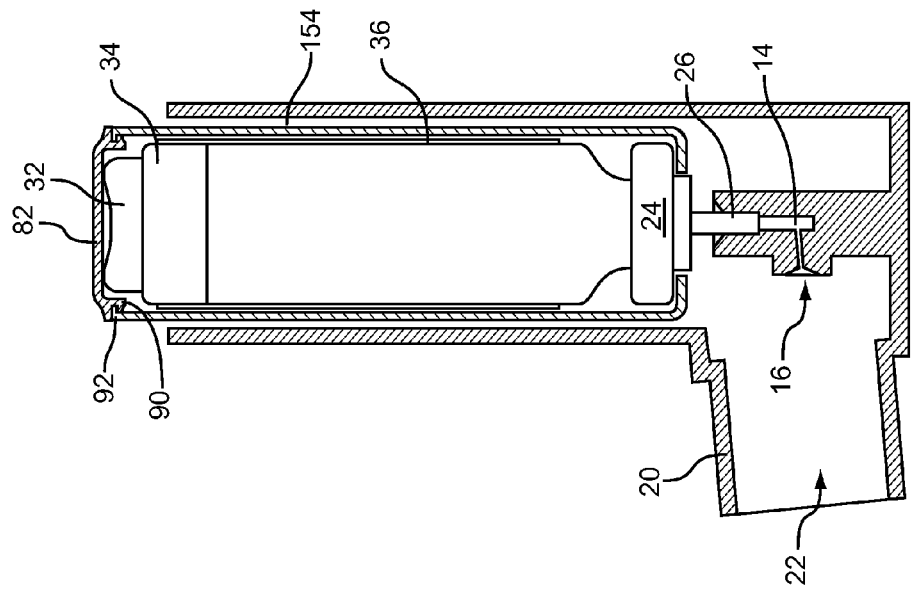
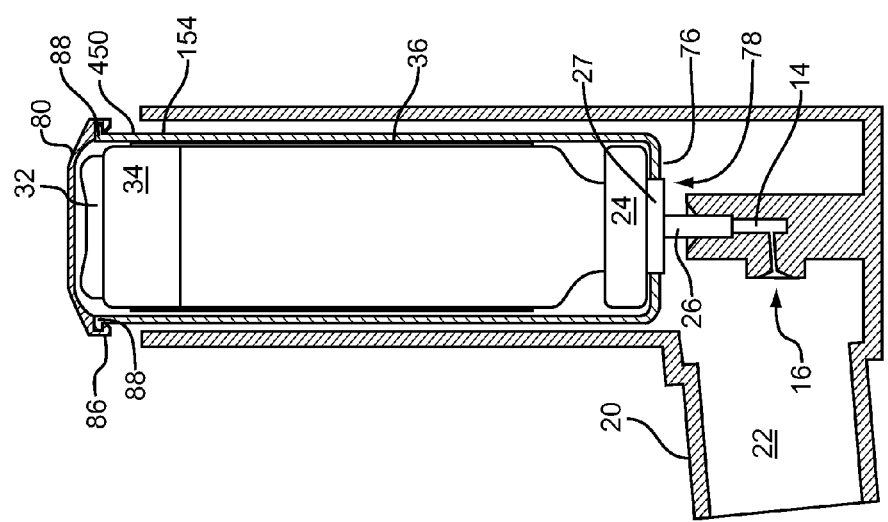
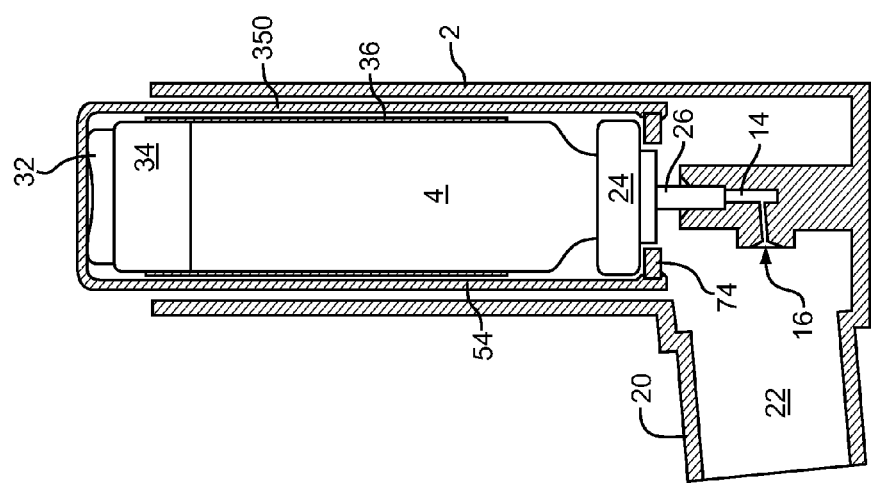

MEDICAMENT DELIVERY SYSTEM WITH DOSE INDICATOR AND OVERSLEEVE ACTUATOR

This application claims the benefit of U.S. Provisional Application No. 61/139,874, filed Dec. 22, 2008 and entitled "Medicament Delivery System With Dose Indicator and Oversleeve Actuator," the entire disclosure of which is hereby incorporated herein by reference.

TECHNICAL FIELD

The present invention relates generally to a medicament delivery system, and in particular, to a medicament delivery system configured with a dose indicator and an oversleeve actuator.

BACKGROUND

Various dispensing devices have been developed where it is desirable to provide information about the number of discharges of a particular substance that have been dispensed from or remain in a container. For example, various aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

In order to provide an accurate indication, some devices are provided with a dose indicator secured to an end of the container, with an actuation force being applied to the dose indicator so as to actuate the dose indicator and the container. In such a system, the force required to actuate the dose indicator must be tuned such that it is not greater than the force required to actuate the container, which could result in an uncounted actuation. Conversely, the force required to actuate the dose indicator cannot be so minimal as to count an actuation when such an event has not transpired.

Some dose indicator devices include a first member (e.g., a cap member) moving along an axis relative to a second member (e.g., a base member secured to the container) in response to a force applied to the first member. In some embodiments, one of the cap or base members has a center post received in a corresponding socket of the other member. If the force applied to the first member is radially spaced (off-center) from the axis, the first member may tilt relative to the second member, which can then cause an increase in friction, for example along the center post or between nested, circumferential walls of the first and second members. This friction force, in turn, increases the force required to actuate the dose counter, which may then not be tuned with the actuation force of the corresponding container. Likewise, an off-axis force application and associated tilting of the cap member can cause the geometrical relationship between internal components, such as ratchet/pawl mechanism, to change, thereby delaying the actuation, which can also adversely affect the relationship between actuation of the container and of the dose indicator. As such, the need remains for an actuator that minimizes the adverse impact from off-axis force applications.

SUMMARY

In a first aspect, a delivery assembly for dispensing a medicament from a container includes a dispenser housing having a support block with a well and an orifice communicating with the well. The dispenser housing includes a longitudinally extending peripheral wall defining an interior surface. A container includes a canister having first and second ends and an exterior surface. The container further includes a valve stem extending from the first end thereof, with the valve stem shaped to be received by the well. The canister is reciprocally moveable along a longitudinal axis defined by the valve stem. The exterior surface of the canister is spaced from the interior surface of the dispenser housing so as to form a gap therebetween. A dose indicator is disposed on the second end of the canister and includes dosage indicia. A sleeve is disposed over the dose indicator and includes a longitudinally extending wall disposed in the gap between the interior surface of the dispenser housing and the exterior surface of the canister. The sleeve is reciprocally moveable relative to the canister and to the dispenser housing.

In another aspect, a medicament delivery kit includes the dispenser housing, the dose indicator and the sleeve. In one embodiment, the kit further includes an adhesive wrap member adapted to secure the dose indictor to the container.

In yet another aspect, a method for dispensing medicament from a medicament delivery device includes moving the sleeve relative to the canister and thereby actuating the dose indicator and moving the sleeve relative to the dispenser housing and thereby moving the canister relative to the support block and dispensing a dosage of medicament from the container.

In yet another aspect, a method for assembling a medicament delivery device includes securing a dose indicator to a container, inserting a valve stem of the container in a well formed in a support block of a dispenser housing, disposing a sleeve over the dose indicator and at least a portion of the canister, and inserting a longitudinally extending wall of the sleeve in a gap between the interior surface of the dispenser housing and the exterior surface of the canister.

The various aspects and embodiments provide significant advantages relative to the prior known devices. In particular, the interface between the longitudinal wall of the sleeve and the canister and/or dispenser housing lengthens the guidance for the actuation of the dose indicator and container, especially when compared with the relatively short length of guidance associated with the internal component interface of the dose indicator alone. As such, the friction forces are greatly reduced during actuation, thereby providing for a more precise tuning between the actuation of the dose indicator and the actuation of the medicament container. In addition, in one embodiment wherein the sleeve is separate from the dose indicator, the control surface for the off-axis force application is separate from the dose indicator actuator, such as the cap, which allows for the tolerances of the dose indicating mechanism to be loosened without a corresponding degradation of tuning between the two actuations.

In addition, the sleeve protects the dose indicator, as well as an adhesive wrap used to secure to the dose indicator to the container in some embodiments. Since the wrap is often configured with instructional indicia, such as prescription data, the sleeve preserves the readability of the instructional indicia while also avoiding potential tampering and damage to the wrap. In addition, the sleeve protects the wrap, for example from tampering with a sharp tool, and prevents the dose indicator from being removed from the container. In an alternative embodiment, the sleeve can also be configured to secure the dose indicator to the container, thereby obviating the need for the adhesive wrap.

The sleeve, in one embodiment, also protects the display of the dose indicator, and prevents tampering with the display, the dosage indicia disposed on the display and/or the internal mechanism of the dose indicator. The sleeve, which is transparent in one embodiment, also can be configured to include a magnifying lens over the display surface such that the dosage indicia are enlarged and easier to read for the user. The sleeve also can be configured to be permanently attached to one of the dose indicator or the container, there preventing removal of the sleeve and preserving the various protections set forth herein.

BRIEF DESCRIPTION OF THE DRAWINGS

FIG. 1 is a perspective view of a first embodiment of a medicament delivery system including a dispenser housing, container, indicating device and oversleeve.

FIG. 2 is a cross-sectional, side view of the first embodiment of a medicament delivery system.

FIG. 3 is a cross-sectional, side view of a second embodiment of a medicament delivery system.

FIG. 4 is a cross-sectional, side view of a third embodiment of a medicament delivery system.

FIG. 5 is a cross-sectional, side view of a fourth embodiment of a medicament delivery system.

FIG. 6 is a cross-sectional, side view of a fifth embodiment of a medicament delivery system.

FIG. 7 is a cross-sectional, side view of a sixth embodiment of a medicament delivery system.

FIG. 8 is a cross-sectional, side view of a seventh embodiment of a medicament delivery system.

DETAILED DESCRIPTION OF THE DRAWINGS

Figure 9:
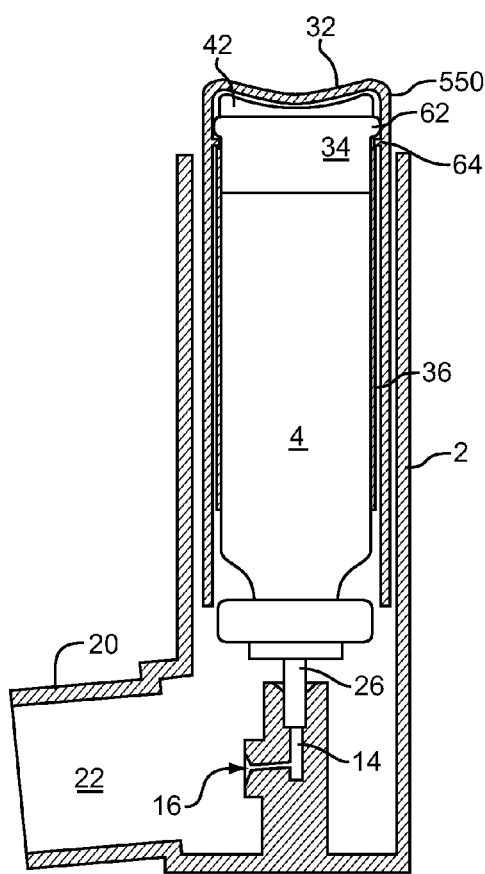
FIG. 9 is a cross-sectional, side view of an eighth embodiment of a medicament delivery system.

Referring to the drawings, and in particular FIGS. 1 and 2, an aerosol dispenser is shown as including a housing 2, or actuator boot, and a container 4 disposed therein. The housing has a longitudinally extending cavity 6 shaped to receive the container. A top portion of the housing is generally open such that the container can be inserted in the housing through opening 8 and be installed therein with a bottom end 10 of the container disposed adjacent the opening so as to be accessible to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIGS. 1 and 2.

As shown in FIG. 2, a cylindrical support block 12 having a well 14 is formed in a bottom portion 18 of the housing. An orifice 16 penetrates the support block to communicate with a bottom portion of the well. In one embodiment, a mouthpiece 20, intended for insertion into the mouth of a patient, forms an exhaust port 22 that communicates with the orifice and well. The mouthpiece 20 extends laterally from the housing so as to facilitate insertion of the mouthpiece into the mouth of the patient.

The container 4 is cylindrical and has a hub 24 disposed on a top thereof. A valve stem 26 extends longitudinally from the hub. The valve stem extends coaxially from the container and is biased outwardly therefrom by a spring (not shown) mounted within the valve stem of the container. The container 4 is mounted in the housing by press fitting the valve stem 26 in the well 14 of the support block.

In a preferred embodiment, the container 4 is filled with a pressurized medicament which is dispensed therefrom in specific metered doses by an actuation thereof effected by depressing or moving the valve stem 26 from an extended closed position to a depressed open position. A single metered dose is dispensed from the container by each reciprocal, longitudinal movement of the valve stem, or actuation of the container.

In operation, the opening of the valve stem is effected by moving the container 4 reciprocally within the housing 2 along a longitudinal axis, defined by the valve stem and the reciprocal movement of the container, by depressing the bottom end 10 of the container relative to the housing 2 so as to move the valve stem 26 to the open position as it is supported within the well by the support block. As the valve stem is moved to the open position, the container dispenses a metered dose of aerosol and medicament through the well 14 and orifice 16. The aerosol and medicament are then transmitted to the patient through the exhaust port 22 of the mouthpiece 20 by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container.

In either embodiment, the metered dose of medicament in aerosol is first dispensed from the container into the chamber, and thereafter inhaled by the patient.

In a preferred embodiment, the container 12 is intended to dispense a predetermined number of metered doses of medicament upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament. It should be understood that other dispensing devices, other than aerosol devices, are configured to sequentially dispense substances, including without limitation other medical dispensing devices such as powder inhalers and other dispensers.

Figure 11:
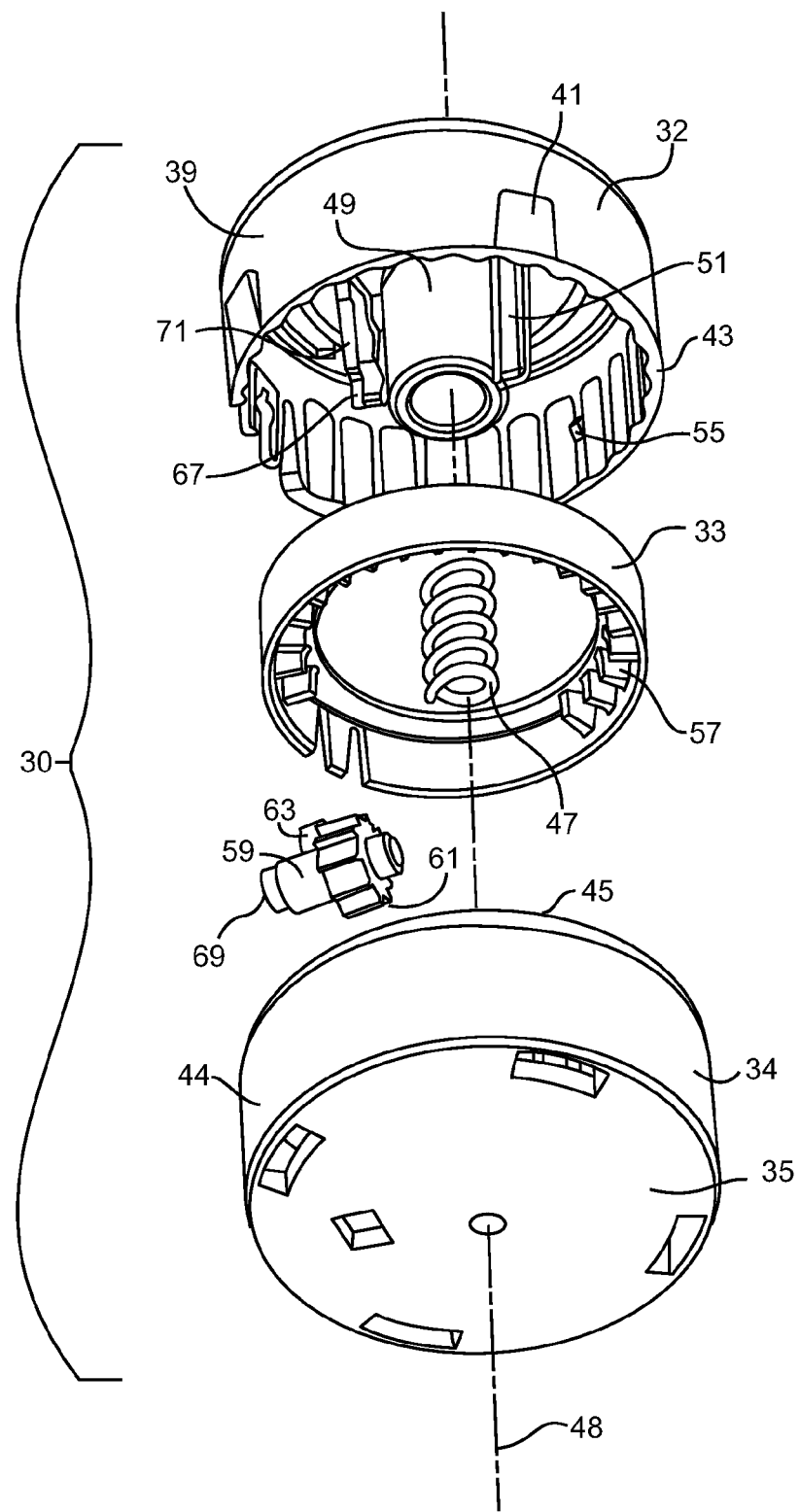
FIG. 11 is an exploded view of an indicating device.

Now generally referring to the FIGS. 1-9, a dispenser indicating device is shown. The indicating device 30 indicates, for example, the number of metered doses that have been dispensed from or remain in the container. As shown in the embodiment of FIGS. 1 and 11, respectively, the indicating device 30 includes an indicating device housing having a first housing component, shown as a cap member 32, disposed in a second housing component, shown as a base member 34. It should be understood that the terms "first" and "second" can be used interchangeable, with the base member referred to as a first housing component and the cap member as a second housing component. The base member 34 is configured such that it can be mounted to the bottom end 10 of the container 4. In one embodiment, the base member 34 includes a convex, or curved bottom portion 35, or floor, which is shaped to be received in and to mate with the bottom end 10 of the container, which has a concave or inwardly curved contour. In various embodiments, the base member 34 is bonded to the bottom of the container with adhesive, double sided tape, or similar bonding agent. In one embodiment, an adhesive wrap 36, such as a label, is wrapped around the indicating device and container, which in one embodiment have substantially the same outer diameter. The label is configured in some embodiments with instructional indicia, for example about how to use the dispensing device or about the medicaments, including for example and without limitation prescriptive information such as instructional indicia about the contents, dosages (quantity and frequency), etc. In other embodiments (not shown), the base member can be configured with a downwardly depending circumferential skirt, which is shaped to receive the bottom end of the container. In such an embodiment, the base member is mounted on the container either by bonding one or more of the bottom portion or skirt to the container, and/or by press fitting the container in the base member so as to provide an interference fit between the container and the depending skirt.

Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section. In addition, it should be understood that the base member can be moveably received in the cap member. Various indicating devices are shown in U.S. Pat. Nos. 7,004,164, issued Feb. 26, 2006, and U.S. Pat. No. 6,729,330, issued May 4, 2004, the entire disclosures of which are hereby incorporated herein by reference.

As best shown in FIGS. 1 and 11, the cap member 32 has a top portion 38 with a viewing window 40 formed therein. Preferably, the cap member 32 is circular in cross-section and the viewing window is formed in the top portion adjacent the outer periphery of the cap member so as to overlie indicia applied to at least one indicator member 42 supported beneath the cap member. The viewing window 40 can be configured in a number of various shapes. For example, the viewing window can be tapered, arcuate shaped (bounded by coaxial inner and outer curved borders and radial side borders), or any other suitable shape. The top of the cap member can be configured with a plurality of raised portions forming a grippable pattern for the user's thumb, or finger. Such features can also be incorporated into a sleeve component 50 (oversleeve), which is disposed over the cap. In this way, the user can firmly press down on the cap member or sleeve component without slippage. One of skill in the art should recognize that other patterns or grippable surfaces, such as a knurled pattern, can be applied to the cap member or sleeve component to facilitate the use of the indicating device. In addition, the viewing window can be formed in one or both of the cap member and base member, for example and without limitation in a side wall/skirts thereof, and also in the sleeve component, the top of which, and in one embodiment the entirety of which, is preferably configured as a see-through or clear material such that the indicator can be seen therethrough.

The cap member 32 includes a circumferential skirt 39 depending downwardly from the top portion 38. The skirt preferably has a smaller diameter than an upwardly depending skirt 44 of the base member, such that the cap member skirt nests within the upwardly extending skirt of the base member. Alternatively, the cap member can be configured with a skirt having a larger diameter than the skirt of the base member such that the base member skirt nests in the cap member skirt as shown in FIG. 9. The cap member 32 is moveably mounted to the base member 34, for example by way of a snap fit. In this way, the cap member 32 is moveable with respect to the base member 34 along an axial, or longitudinal, path.

The axial movement of the cap member 32 relative to the base member 34 is bounded or constrained by the engagement of engagement members 41 on one or the other of the cap member and base member with recess, lip 45 or engagement members on the other of the cap member and base member at a fully extended position and by engagement of a bottom rim 43 of the cap member skirt with a surface of the bottom portion of the base member at the bottom of the stroke, or by engagement of the top of the skirt of the base member on the bottom of the cap member. One of skill in the art should understand that the engagement members can alternatively be formed on the base member skirt so as to engage pockets or openings, or a rim (or like protrusion), formed on the cap member skirt.

A spring 47 is disposed between the cap member and the base member. The spring is preferably disposed around or within an upwardly extending hub portion of the base member, which mates with a post 49 extending downwardly from the top portion of the cap member, with the hub and post portions functioning as guide members. The hub and port portions can be configured with corresponding key portions 51, which prevents relative rotation between the cap member and base member, thereby ensuring proper engagement of the drive mechanism. The spring 47 functions as a return mechanism and biases the cap member upwardly away from the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

A first indicator member 33 is rotatably mounted in the cap member 32 about a longitudinal axis 48 substantially parallel to the axial movement of the cap member relative to the base member, and preferably coaxially therewith. It should be understood that more than one indicator member, as disclosed for example in U.S. Pat. No. 6,729,330, the entire disclosure of which is hereby incorporated herein by reference, may also be used. The indicator member is also referred to herein as a driven member. The indicator member is generally open in the middle and includes an annular ring portion having an upper surface that rotatably slides along a bottom surface of the top portion of the cap member 32. Alternatively, the indicator member can be mounted on the outside of the cap member with a viewing window formed in the indicator member for viewing indicia applied to the top of the cap member.

The indicator member is rotatably secured to the cap member with a plurality of protrusions 55 or tab members, which extend from an inner circumferential surface of the cap member skirt. Alternatively, the indicator member can include an engagement member, or rim, that engages a groove or similar opening in the cap member. In this way, the indicator member is secured to the cap member so as to prevent axial movement therebetween but wherein the indicator member 33 is permitted to rotate relative to the cap member 32. The indicator member is installed by snap-fitting the indicator member within the cap member. One of skill in the art should understand that the indicator member could alternatively be rotatably mounted on the cap member hub portion, or on a similar axle secured to the cap member.

The indicator member 33 has a plurality of teeth 57 formed around the outer periphery on a bottom side of the annular ring member. Dosage indicia 46 in the form of numbers, characters, text and/or color codings, or combinations thereof, are provided on the top surface of the indicator member and are visible to the user through the viewing window 40 provided in the top of the cap member.

In one embodiment, the indicia are configured as numbers arranged sequentially from 0 to 200 around the upper surface of the indicator member. It should be understood that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid displayed in the viewing window could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container should be replaced, or, conversely, to go from the starting predetermined number to 0 (or some ending number), which again indicates to the user that the container should be replaced.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel. In various preferred alternative embodiments, one or both of the base member and cap member can be made of polycarbonate.

A drive mechanism is shown as including a drive assembly 59. The drive assembly includes a ratchet wheel 61 coaxially mounted to a drive member on an axle 69. The ratchet wheel, drive member and axle can be made separately, with the ratchet wheel and drive member then mounted on the axle, or all three parts can be integrally molded as a one-piece component. The drive assembly is preferably made of hard plastic material such as Acetel. In one embodiment, the drive assembly further includes a second dosage indicator member (not shown) coaxially mounted with and between the drive member and ratchet wheel. The indicator member is configured as a wheel and preferably includes dosage indicia positioned around the peripheral surface thereof. Preferably, the indicia are comprised of consecutive numerals running from 0 to 9, and provide dispensing indicia to the user in combination with indicator member 33.

The ratchet wheel includes a plurality of teeth (preferably ten) formed around its periphery. Each of the teeth includes an engagement surface and a tapered surface. The drive member, whether integrally formed with the ratchet wheel or separately connected thereto, includes a single tooth 63 extending radially from the axle.

The drive assembly is mounted to the cap member by engaging opposite ends of the axle 69 with downwardly extending hub portions 67 such that the axle, ratchet wheel and drive member rotate about an axis substantially perpendicular to the axial movement of the cap member relative to the base member and to the axis of rotation of the indicator member. Alternatively, the drive assembly can be mounted to the base member, along with the indicator member, in a similar manner.

The drive mechanism further includes a pawl member (not shown), which extends upwardly from the bottom portion of the base member and selectively engages one of the teeth of the ratchet wheel 61. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member 71, flexible rod or finger, extends downwardly from the top portion of the cap member and selectively engages another of the teeth of the ratchet wheel. It should be understood that the pawl member could alternatively extend from the cap member (and the non-return member from the base member) when the drive assembly is mounted to the base member, as described above. Of course, when formed integrally with one or the other of the cap member and base member, the pawl member and non-return member are preferably made of the same materials as the respective cap member and base member.

In operation, the user depresses the cap 32 member from a fully extended position toward the base member such that the cap member bottoms out in the base member at the bottom of the stroke and such that the base member imparts an axial load on the container until a metered dosage is dispensed therefrom. In a preferred embodiment, the biasing force of the spring 47, or alternative return mechanism such as resilient arm members which act as springs as the arm members slide along ramped biasing surfaces, is less than the biasing force of the spring located in the metering valve of the container, such that the cap member first bottoms out in the base member with the container then being moved downwardly in the housing until a metered dose is dispensed.

As the cap member 32 is depressed toward the base member 34, the pawl selectively engages and rotates the ratchet wheel teeth, while the non-return member is biased outwardly until it selectively engages the next tooth near the bottom of the stroke. The non-return member provides an audible click as it engages the next tooth. The user then releases the cap member whereinafter the spring, or similar return mechanism, biases the cap member 32 away from the base member 34. When the cap member is released by the user, the container is biased upwardly within the housing along the longitudinal axis such that the valve stem 26 is moved to the closed position within the container. Simultaneously, as the cap member 32 is released and allowed to move away from the base member 34, the pawl is biased outwardly by the ratchet wheel as the non-return member prevents a backwards rotation thereof so as to maintain a unidirectional rotation of the ratchet wheel. At the top of the stroke, the pawl is again placed in position for selective engagement with one of the teeth of the ratchet wheel. Again, the pawl provides an audible click as it engages the next tooth. In summary, on the down stroke the non-return member makes a clicking sound as it slides over one or more ratchet teeth, while on the up stroke, the pawl member also makes a clicking sound as it slides over one or more ratchet teeth. In this way, the ratchet wheel, and connected drive member, are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel 61 will make one full revolution for every ten actuations of the indicator device and container, or a tenth of a revolution for each actuation. It should be understood that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl is biased outwardly by the tapered surface of one of the ratchet wheel teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

In one embodiment, the drive member has a single tooth 63 or segment. Therefore, upon every tenth actuation, the drive member is rotated such that the tooth selectively engages one of the teeth formed on the indicator member so as to rotate the indicator member 33 an incremental amount. The incremental amount of rotation is defined by the distance between adjacent teeth, otherwise defined as the circular pitch of the teeth. In this way, the drive member is selectively engaged with at least one of the teeth of the indicator member after and upon a predetermined number of axial movements of the cap member relative to the base member so as to rotate the indicator member the incremental amount. The predetermined of number axial movements required to cause the indicator member to rotate is defined by and dependent upon the reduction ratio of the ratchet wheel and drive member, which, in turn, is defined by dividing the number of teeth formed on the ratchet wheel by the number of teeth formed on the drive member. For example, as shown in the preferred embodiment, a ratchet wheel having ten teeth and a drive member having one tooth will result in an incremental movement of the indicator member, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

In one embodiment, the ratchet wheel 61 includes ten teeth. As the container is actuated ten times, the drive tooth 63 rotates around until it engages one of the teeth 57 on the indicator member. At this point, the drive member has completed a single cycle equal to the number of predetermined number of axial movements, which results or culminates in the incremental movement of the indicator member. The cycle is then repeated (by again making the predetermined number of axial movements) so as to again culminate in the incremental movement of the indicator member. Preferably, numerical indicia (tens counter) are applied so as to correlate to the preferred embodiment requiring ten axial movements for one incremental advancement of the indicator wheel, with numerical indicia 0-9 applied to the outer peripheral surface of the second indicator member, if used.

The ratchet wheel and drive member with their reduction ratio provide a simple but reliable mechanism for advancing the indicator member. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member. As such, the indicator member 33 can be made with coarser teeth at less cost. In addition, larger coarser teeth interacting with a relatively large drive member tooth helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses). This single revolution corresponds to a usage cycle, which is defined as the movement of the dosage indicator from an initial reading, which indicates that the container is full, to a final reading, which indicates that the container should be replaced. Of course, the indicator member, if initially set to a smaller number of dosages, may make less than a complete revolution in completing a usage cycle.

It should be understood that the indicator member or members could also be rotatably mounted to the base member, along with the drive mechanism, with the pawl extending from the cap member. In essence, either the cap member ore the base member can directly support the indicator member (s), which is/are disposed between the cap member and base member. It should also be understood that one, two, or even more indicator members can be used to provide dosage indicia to the user.

The viewing window 34 can be configured large enough such that the dosage indicator member 33, and a second dosage indicator member if used, with their indicia are visible therein. In the operation of a second embodiment, a second indicator member rotates with each actuation of the cap member 32 relative to the base member 32 as the ratchet wheel is driven by the pawl member. The indicator member rotates about an axis substantially perpendicular to the axial movement of the cap member relative to the base member and to the rotational axis of the indicator member. In the preferred embodiment, with the indicator member having "ones" indicia and the ratchet wheel having ten teeth, the indicator member is advanced upon each actuation and provides indicia visible to the user to notify them of such advancement. As the indicator member completes a cycle, or rotation, the indicator member 33 is advanced one increment by the drive member and the indicator member begins another cycle. In this way, the user is advised as to each actuation of the indicating device and the attendant dispensment of a dosage from the attached container.

As shown in FIG. 2, the upper surface of the first housing component is relatively flat, or even concave. Ordinarily, the user actuates the indicating device by applying a force (e.g., depressing) to the cap member at a location spaced from the center longitudinal axis 48, which is aligned with the return spring. The off-center load, however, can lead to a tilting of the cap member relative to the base member due to the moment of the applied and resistant longitudinal forces. This tilting can lead to the center guide post bending, which further leads to a frictional force between the guide post and corresponding socket formed in the post, as well as create a friction force on opposite sides between the respective skirts or walls of the cap member 32 and base member 34. In addition, the coefficient of friction in plastics can increase with increased normal forces, thereby increasing the frictional forces resisting movement between the first and second housing components. This friction force, in turn, increases the force required to actuate the indicating device, which may then not be tuned with the actuation force of the corresponding container 4. As such, the container 4 may actuate without a corresponding actuation of the indicating device, thereby leading to an inaccurate counting of dispensed or remaining dosages.

Referring to FIGS. 2-8, a sleeve 50 is disposed over the dose indicator. The sleeve 50 includes a top 52 and a longitudinally extending, circumferential wall 54 disposed in a gap 56 between an interior surface 58 of the dispenser housing and an exterior surface 60 of the container, or canister portion thereof, or wrap 36. The increased length of the sleeve wall 54, as compared with the relative depth of the cap member 32 relative to the base member 34, provides increased guidance for the indicating device and results in greatly reducing the tilting of the cap member relative to the base member, and the attendant disadvantages associated therewith. In addition, by removing the control surface for the tilting to a point significantly removed from the component that needs controlling, the tolerances can be lessened while still maintaining a tighter control. In various embodiments, the wall 54 of the sleeve is at least 2.52 inches long (L1), or includes at least 0.945 inches in overlap between the wall and the wall of the dispenser housing when the container is in an at-rest or non-dispensing position. In some embodiments, the wall 54 has a length proximate the overall length of the container. In some embodiments, the length (L1) of the wall and sleeve 50 is between about 50% and 80% of the length (L2) of the container 4 (excluding the valve stem) and indicating device 30 (measured to the top of the cap member).

In general, the sleeve 50 is reciprocally moveable relative to the canister 4, and also is reciprocally moveable relative to the dispenser housing 2.

In various embodiments, the sleeve is either secured to the indicator device, including one or the other of the cap member and base member, or to the container. In various embodiments, the sleeve 50 is moveably, fixedly secured to the indicating device 30 or container 4, for example with a snap fit, such that the sleeve can be moved relative to the container with an actuation of the indicating device and container.

In those embodiments where an adhesive wrap 36 is used to secured the indicating device to the container, the wall 54 of the sleeve is disposed between the outer surface 60 of the wrap and the interior surface 58 of the dispenser housing. In this way, the sleeve protects the wrap or label 36 and preserves the indicia applied thereto, while also preserving and protecting the joint between the container and the indicating device. Likewise, the sleeve 50 protects, and prevents tampering with, the indicating device 30. In other embodiments, the sleeve itself secures the indicator to the container, such that the adhesive wrap, or other coupling device, can be omitted.

In the embodiments of FIGS. 2-8, the sleeve 50, 150, 250, 350, 450 is configured either with a viewing window that is aligned with the viewing window in the cap member, with the sleeve being secured such that the sleeve is not rotatably relative to the cap member, for example with an engagement member. Alternatively, the top 52 of the sleeve, or in one embodiment the entirety of the sleeve, is made from a clear material, such a polymer or plastic, such that the indicator member 42 and indicia 46 applied thereto, are easily visible through the sleeve. The top 52 can be further shaped or configured as a magnifying lens, such that the indicia 46 on the indicator member beneath the sleeve are enlarged when viewed through the top and thereby made easier to read for the user. The top 52 of the sleeve can be configured with a contoured surface, e.g., concave or convex, grippable portions such as ribs or a knurled surface.

Referring to the embodiment of FIG. 2, the sleeve 50 is secured to the base member 34, which includes a peripheral rim 62, with a snap fit employing one or more lugs 64, or a peripheral lug or rim. In this way, the sleeve 50 is fixedly secured to the indicating device 30, and the base member 34 in particular so that the sleeve cannot be disengaged therefrom. At the same time, the sleeve 50 is reciprocally moveable with the cap member 32 relative to the base member 34, container 4 and dispenser housing 2, and after the cap member 32 bottoms out in the base member 34, the sleeve 50 is reciprocally moveable with the container 2 and indicating device 30 relative to the dispenser housing 2. The snap fit of the sleeve can be effected during a first actuation of the container. It should be understood, especially where at least the top of the cap member is clear, that the sleeve can rotate about the axis 18 relative to the cap member and container.

To assemble a kit for the overall device, the indicating device 30 is first secured to the container 4, for example with a wrap 36. The container 4 is then be engaged with the dispenser housing 2, for example by disposing the valve stem 26 in the well 14. The sleeve 50 is then slipped over the indicating device 30 and the sleeve and cap member are depressed until the sleeve 50 is engaged with, but moveable relative to, the base member 34. Of course, the engagement or coupling can be effected before the container is engaged with the dispenser housing.

Referring to the embodiment shown in FIG. 3, the sleeve 150 is coupled to the cap member. In one embodiment, the cap member 32 includes a peripheral lip 66 that is engaged by a snap fit with tabs/lugs 68 or a protrusion (e.g., peripheral lip) on the sleeve. In this embodiment, the sleeve 150 is not longitudinally moveable relative to the cap member 32, but rather is reciprocally moveable with the cap member 32 in a longitudinal direction relative to the base member 34, container 4 and dispenser housing 2.

Referring to the embodiment of FIG. 4, the sleeve 250 is not coupled to the indicating device, but rather includes a flange or lip 70 extending radially inwardly from the bottom of the wall. The lip 70 engages the hub portion 24 of the container with a snap fit, which prevents the sleeve 250 from being removed from the container, but allows the sleeve to move reciprocally with the cap member 32 in a longitudinal direction relative to the base member 34 and container 4, and ultimately relative to the dispenser housing 2.

The embodiments of FIGS. 5 and 6 are similar to the sleeve shown in FIG. 4, except a retention ring 72, 74 is secured to the inner portion of the wall 54 of the sleeve 350. The ring 74 is disposed adjacent the end of the container as shown in FIG. 6, or the ring 72 is disposed in the recess formed by the neck of the container as shown in FIG. 5. The retention ring 72, 74 is secured to the wall 54 of the sleeve with a snap-fit, welding, bonding, adhesive, mechanical fasteners, or combinations thereof.

FIGS. 7 and 8 are similar to the sleeve shown in FIG. 4, except the sleeve 450 has a bottom 76 with an opening 78 through which the valve stem and hub portion 27 are disposed. A top member 80, 82 is then secured to the sleeve walls 154 at a top edge thereof. For example in FIG. 7, the top member 80 and wall 154 are configured with mating elements 86, 88 providing for an internal snap-fit that is difficult to tamper with. Alternatively, as shown in FIG. 8, the top member 82 and wall 154 are configured with mating elements 90, 92 forming an external snap fit.

It should be understood that with the embodiments of FIGS. 4-8, the sleeve secures the indicating device to the container, such that the adhesive label, or other coupling devices, can be omitted.

Figure 10:
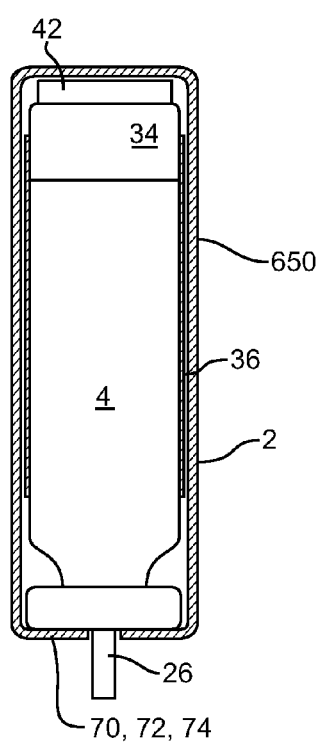
FIG. 10 is a cross-sectional, side view of a ninth embodiment of a medicament delivery system.

Referring to FIG. 9, the sleeve 550 and cap member are integrated into a single sleeve member. The sleeve is disposed over the dose indicator, which includes the indicator member 42 and base 34, and is secured to the base as described above with respect to FIG. 2, including lugs 64 engaging a rims 62, such that the sleeve can move relative to the base member. The sleeve is configured with various hubs and other devices to secure the drive mechanism and indicator thereto as described above with respect to the cap member. The sleeve can be coupled to the base member, after the base member is secured to the container 4, for example with an adhesive wrap 36. Alternatively, as shown in FIG. 10, the integrated sleeve and cap member 650, referred to as a sleeve member, are secured to the container over the dose indicator components, including the indicator member and the base member, with a flange member 70, or retention ring 72, 74. The cap member can be secured to the container using any of the configurations of FIGS. 4-8.

Various indicating devices and components thereof are disclosed in U.S. Pat. Nos. 6,082,358, 6,336,453 and 6,328,037, all of which are hereby incorporated herein by reference. Although the indicating device has been described herein in connection with an aerosol container, it should be understood that it can be used with other dispensing devices which are actuated, with each actuation causing a movement of the drive member.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A delivery assembly for dispensing a medicament from a container comprising:
    a dispenser housing comprising a support block having a well and an orifice communicating with said well, said dispenser housing comprising a longitudinally extending peripheral wall defining an interior surface;
    a container comprising a canister having first and second ends and an exterior surface, said container further comprising a valve stem extending from said first end of said container and shaped to be received by said well in said support block, said canister being reciprocally moveable along a longitudinal axis defined by said valve stem, said exterior surface of said canister spaced from said interior surface of said dispenser housing so as to form a gap therebetween;
    a dose indicator disposed on said second end of said canister, said dose indicator comprising dosage indicia; and
    a sleeve disposed over said dose indicator and comprising a longitudinally extending wall disposed in said gap between said interior surface of said dispenser housing and said exterior surface of said canister, wherein said sleeve is reciprocally moveable relative to said canister and is reciprocally moveable relative to said dispenser housing.

2. The delivery assembly of claim 1 further comprising an adhesive wrap member securing said dose indicator to said container, said adhesive wrap member adhered to said exterior surface of said container and an exterior surface of said dose indicator, wherein said sleeve wall is disposed between an exterior surface of said adhesive wrap member and said interior surface of said dispenser housing.

3. The delivery assembly of claim 2 wherein said adhesive wrap member comprises instructional indicia.

4. The delivery assembly of claim 1 wherein said sleeve comprises a viewing window, wherein said dosage indicia are visible through said viewing window.

5. The delivery assembly of claim 4 wherein said viewing window comprises a transparent portion of said sleeve.

6. The delivery assembly of claim 1 wherein said dose indicator comprises a base member disposed on said second end of said canister and said sleeve comprises a cap member disposed over said base member.

7. The delivery assembly of claim 1 wherein said dose indicator comprises a base member disposed on said second end of said canister and a cap member reciprocally moveable relative to said base member, and wherein said sleeve comprises an end portion disposed over said cap member.

8. The delivery assembly of claim 7 wherein said sleeve is moveably secured to said base member such that said sleeve is moveable relative to said base member along said longitudinal direction.

9. The delivery assembly of claim 7 wherein said sleeve is fixedly secured to said cap member such that said sleeve is moveable with said cap member relative to said base member along said longitudinal direction.

10. The delivery assembly of claim 1 wherein said sleeve is moveably secured to said first end of said canister such that said sleeve is moveable relative to said canister along said longitudinal direction.

11. The delivery assembly of claim 10 wherein said sleeve is moveably secured to said first end of said canister with a snap-fit connection.

12. The delivery assembly of claim 10 wherein said sleeve is moveably secured to said first end of said canister with a retention collar.

13. The delivery assembly of claim 1 wherein said sleeve comprises an end portion secured to a peripheral wall portion with a snap fit.

14. A medicament delivery kit adapted to be assembled and dispense medication from a container, the kit comprising:
    a dispenser housing comprising a support block having a well and an orifice communicating with said well, said dispenser housing comprising a longitudinally extending peripheral wall defining an interior cavity, wherein said well is shaped and adapted to engage a valve stem of the container;

a dose indicator configured for connection to the container, said dose indicator comprising dosage indicia; and a sleeve adapted to cover said dose indicator, said sleeve comprising a longitudinally extending wall dimensioned to be disposed in said interior cavity of said dispenser housing, wherein said sleeve is adapted to be reciprocally moveable relative to the canister and is adapted to be reciprocally moveable relative to said dispenser housing.

15. The kit of claim 14 further comprising an adhesive wrap member adapted to secure the dose indicator to the container.

16. The kit of claim 14 wherein said sleeve is secured to said dose indicator.

17. A method for dispensing medicament from a medicament delivery device comprising:

providing a dispenser housing comprising a support block having a well and an orifice communicating with said well, said dispenser housing comprising a longitudinally extending peripheral wall defining an interior surface;

providing a container comprising a canister having first and second ends and an exterior surface, said container further comprising a valve stem extending from said first end of said container and received in said well in said support block, wherein said exterior surface of said canister is spaced from said interior surface of said dispenser housing so as to form a gap therebetween;

providing a dose indicator disposed on said second end of said canister, said dose indicator comprising dosage indicia;

providing a sleeve disposed over said dose indicator and comprising a longitudinally extending wall disposed in said gap between said interior surface of said dispenser housing and said exterior surface of said canister;

moving said sleeve relative to said canister and thereby actuating said dose indicator; and moving said sleeve relative to said dispenser housing and thereby moving said canister relative to said support block and dispensing a dosage of medicament from said container.

18. The method of claim 17 wherein said moving said sleeve relative to said canister occurs simultaneously with or before said moving said sleeve relative to said dispenser housing.

19. A method of assembling a medicament delivery device comprising:

securing a dose indicator to a container comprising a canister having first and second ends and an exterior surface;

inserting a valve stem of said container in a well formed in a support block of a dispenser housing, wherein an exterior surface of said canister is spaced from an interior surface of said dispenser housing so as to form a gap therebetween;

disposing a sleeve over said dose indicator and at least a portion of said canister; and inserting a longitudinally extending wall of said sleeve in said gap between said interior surface of said dispenser housing and said exterior surface of said canister.

20. The method of claim 19 further comprising securing said sleeve to said dose counter.

21. The method of claim 20 wherein said dose counter comprises a base member secured to said canister and a cap member moveably connected to said base member, wherein said securing said sleeve to said dose indicator comprises securing said sleeve to said cap member.

22. The method of claim 20 wherein said dose counter comprises a base member secured to said canister and a cap member moveably connected to said base member, wherein said securing said sleeve to said dose indicator comprises securing said sleeve to said base member.

23. The method of claim 19 further comprising securing said sleeve to said container.

24. The method of claim 23 wherein said disposing said sleeve over said dose indicator and said at least a portion of said canister and said securing said sleeve to said container both occur prior to said inserting said valve stem of said container in said well.

25. The method of claim 19 wherein said securing said dose indicator to said container comprises wrapping an adhesive wrap member around said dose indicator and said container.

26. The method of claim 19 wherein said sleeve is reciprocally moveable relative to said container.

* * * * *